United States Patent [19]

Miyake et al.

[11] Patent Number: 4,521,252

[45] Date of Patent: Jun. 4, 1985

[54] PROCESS FOR PRODUCING A HIGH-PURITY ISOMALTOSE

[75] Inventors: Toshio Miyake; Shūzō Sakai; Takashi Shibuya, all of Okayama, Japan

[73] Assignee: Kabushiki Kaisha Hayashibara Seibutsu Kagaku Kenkyujo, Okayama, Japan

[21] Appl. No.: 420,702

[22] Filed: Sep. 21, 1982

[30] Foreign Application Priority Data

Oct. 26, 1981 [JP] Japan ................................. 56-171179

[51] Int. Cl.$^3$ ............................ C13D 3/12; C13D 3/14
[52] U.S. Cl. .................................. 127/46.3; 127/46.2; 127/40; 435/96; 435/99
[58] Field of Search ....................... 127/46.2, 46.3, 40; 435/96, 99, 97

[56] References Cited

U.S. PATENT DOCUMENTS

| | | | |
|---|---|---|---|
| 4,022,637 | 5/1977 | Sutthoff et al. | 127/46.2 |
| 4,366,060 | 12/1982 | Leiser et al. | 127/46.2 X |
| 4,384,898 | 5/1983 | Okada et al. | 127/46.3 X |
| 4,391,749 | 7/1983 | Shimizu et al. | 127/46.2 |

OTHER PUBLICATIONS

Whistler et al; Methods in Carbohydrate Chemistry, vol. VIII, Academic Press, N.Y., 1980, pp. 14-19.

*Primary Examiner*—Kenneth M. Schor
*Attorney, Agent, or Firm*—Browdy and Neimark

[57] ABSTRACT

The present invention relates to a process for producing a high-purity isomaltose by applying an aqueous solution, containing isomaltose, to a column packed with a strongly-acidic cation exchange resin of alkali metal- or alkaline earth metal-form; and fractionating by charging water to obtain a high-isomaltose fraction with an isomaltose content of at least 40%, thereby enabling industrial-scale production of a high-purity isomaltose much easier at lower cost.

12 Claims, 1 Drawing Figure

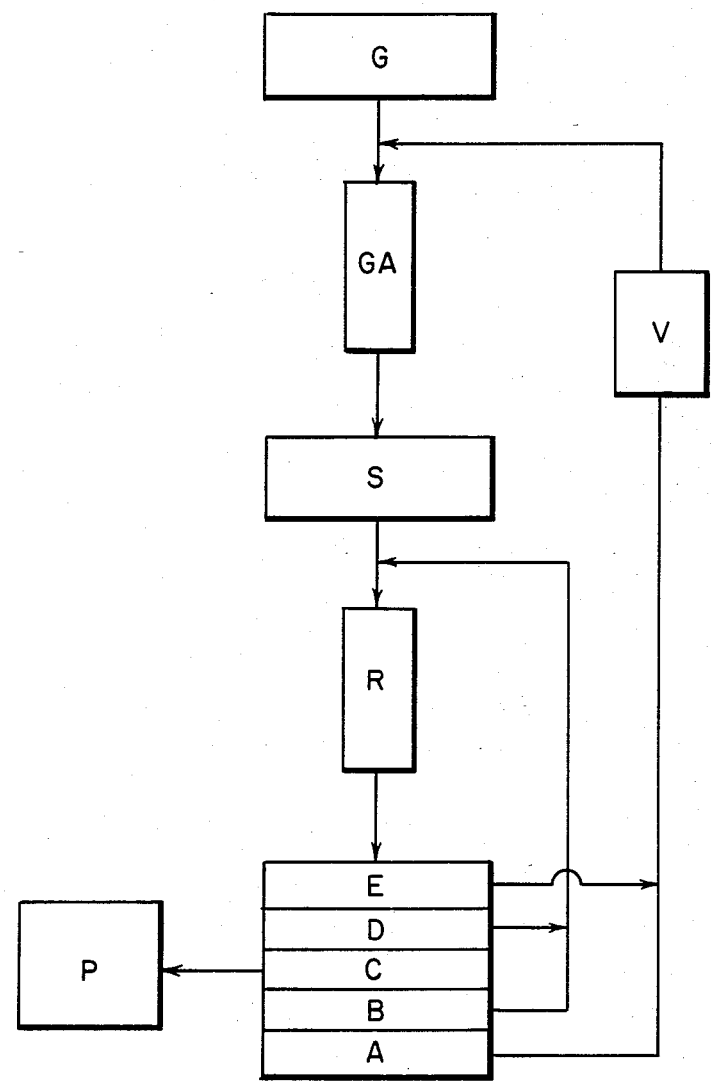

PROCESS FOR PRODUCING A HIGH-PURITY ISOMALTOSE

FIELD OF THE INVENTION

The present invention relates to a process for producing a high-purity isomaltose.

BACKGROUND OF THE INVENTION

It is well documented that isomaltose is a disaccharide with a low-sweetness, found in trace in some food products, e.g., fermented foods, which is obtainable in a substantial amount of up to 10–25 w/w % on dry solid basis (all percentages as used in the SPECIFICATION should mean "weight percentages on dry solid basis" unless specified otherwise) by reversible reaction with the use of acid catalyst or glucoamylase, glucose-transfer reaction of maltose or maltodextrin with the use of α-glucosidase (trans-glucosidase), or partial hydrolysis of dextran.

Early establishment of an industrial-scale and low-cost production of isomaltose material with the highest possible purity has been strongly anticipated because of the recent finding that isomaltitol, a hydrogenated product of isomaltose, is usable as a low-cariogenic and low-caloric sweetener.

SUMMARY OF THE INVENTION

The present inventors have investigated processes for producing a high-purity isomaltose which is feasible on an industrial-scale.

BRIEF DESCRIPTION OF THE DRAWING

The FIGURE shows a flow chart of a process for producing high-purity isomaltose, in accordance with the present invention.

DETAILED DESCRIPTION OF PREFERRED EMBODIMENTS

These efforts resulted in the finding that a great amount of a high-purity isomaltose is easily obtainable by applying a feed sugar solution, containing isomaltose, to a column packed with a strongly-acidic cation exchange resin of alkali metal- or alkaline earth metal-form; fractionating by charging thereto water the solution into high-isomaltodextrin fraction, high-isomaltodextrin·isomaltose fraction, high-isomaltose fraction, high-isomaltose fraction, high-isomaltose·glucose fraction, and high-glucose fraction, in the given order; and recovering the high-isomaltose fraction with an isomaltose content of 40% or higher.

Also, these efforts resulted in the additional finding that the objective high-purity isomaltose is consistently obtainable by employing a method wherein the material sugar solution is applied to the column together with the previously obtained high-isomaltodextrin·isomaltose- and/or high-isomaltose·glucose-fractions, and wherein the resultant high-isomaltodextrin·isomaltose- and/or high-isomaltose·glucose-fractions are applied to the column together with a fresh feed sugar solution in the next fractionation step, enabling an industrial-scale production of a high-purity isomaltose at lower cost.

The terms "high-A fraction" and "high A·B fraction" as used in the specification shall mean the eluted fractions containing A, or A and B as predominant constituent(s) respectively, and the term "isomaltodextrin" shall mean "isomaltodextrins with polymerization degrees higher than that of isomaltose".

These findings led to the present invention.

The feed material sugar solution usable in the invention may be one of those which contains isomaltose, and which gives a high isomaltose fraction with an isomaltose content of 40% or higher in high recovery yield when subjected to fractionation according to the present invention. For example, the feed sugar solution may be, preferably, a reversible-reaction product from glucose obtained with the use of an acid catalyst or glucoamylase (EC 3.2.1.3); glucose-transferred product obtained with the use of α-glucosidase (EC 3.2.1.20); or a partial dextran hydrolysate, but isomaltose contents thereof should be at least 7%.

In the case of preparing the feed sugar solution with the use of glucoamylase, an aqueous solution of certain partial starch hydrolysate, e.g., maltose, maltodextrin, corn syrup, dextrin, or mixtures thereof, generally, concentration of about 40–80 w/w %, may be used instead of an aqueous solution of glucose.

When the feed sugar slution is prepared with the use of α-glucosidase, an aqueous solution of partial starch hydrolysate, e.g., maltose, maltodextrin, corn syrup, dextrin, of mixtures thereof, generally, concentration of about 50 w/w %, to an acid catalyst, and neutralizing the resultant mixture solution; or, alternatively, subjecting the dextran solution to the enzymatic hydrolysis of either dextranase (EC 3.2.1.11) or isomaltodextranase (EC 3.2.1.94).

The strongly-acidic cation exchange resin of alkali metal- or alkaline earth metal-form usable in the invention may be one or more members of styrene-divinylbenzene copolymer resins, for example, bearing sulphonyl group of alkali metal- or alkaline earth metal-form, such as $Na^+$, $K^+$, $Ca^{2+}$ or $Mg^{2+}$. Commercially-available resins are, for example, "Dowex 50WX2", "Dowex 50WX4" and "Dowex 50WX8", products of Dow Chemical Company, Midland, Mich., U.S.A., "Amberlite CG-120", a product of Rohm & Haas Company, Philadelphia, Pa., U.S.A.; "XT-1022E", a product of Tokyo Chemical Industries, Kita-ku, Tokyo, Japan; and "Diaion SK 1B", "Diaion SK 102" and "Diaion SK 104", products of Mitsubishi Chemical Industries Limited, Tokyo, Japan. All of these resins have excellent fractionating capabilities to obtain the high-isomaltose fraction, and are highly heat- and abrasion-resistant; thus, they are advantageously feasible for producing a high-purity isomaltose on an industrial-scale.

In the process according to the present invention, the resin with a nominal particle size of about 0.01–0.5 mm, in an aqueous suspension, is packed in one or more columns. The bed depth preferred in the present invention is 7 m or longer. If two or more columns are used, they are cascaded to give a total bed depth of 7 m or longer.

When a column with a bed depth of shorter than 7 m is used, the fractions may be reapplied to the column in the elution order, and refractionated therein, such that the total contact bed depth of the resin to the material sugar solution reaches 7 m or longer until the high-isomaltose fraction is harvested.

As to the column usable in the invention, any column can be used regardless of its material, size and shape so far the objectives of the invention can be attained therewith. The column may be, for example, of glass, plastic or stainless steel; and its shape is, for example, in cylindrical or square pillar form, but should be devised to give the best possible effective laminar flow when the feed sugar solution is applied to the column packed with the resin.

The following descriptions concretely explain the detailed method to practice the present invention.

After packing the strongly-acidic cation exchange resin of alkali metal- or alkaline earth metal-form, in an aqueous suspension, in one or more columns to give a total bed depth of 7 m or longer, the column(s) is applied with the feed sugar solution, concentration of about 10–70 w/w %, in an amount of about 1–60 v/v % against the bed volume, and then charged upwards or downwards with water at a flow rate of about SV 0.1–2.0 to effect fractionation of the material sugar solution into high-isomaltodextrin fraction, high-isomaltodextrin-isomaltose fraction, high-isomaltose fraction, high-isomaltose-glucose fraction, and high-glucose fraction, in the given order, while keeping the temperature in the column(s) at 45°–85° C., followed by the harvest of the high-isomaltose fraction with an isomaltose content of 40% or higher.

Although the eluates can be collected periodically in every about 1–20 v/v % against the bed volume, they may be distributed automatically into the fractions.

When the feed sugar solution is applied to the column prior to, after, or together with the application of the previously obtained high-isomaltodextrin-isomaltose and/or high-isomaltose-glucose-fractions, the amount of water required for substantial fractionation of the feed sugar solution can be extremely reduced, and the isomaltose constituent in the feed sugar solution can be recovered in higher purity, higher concentration, and higher recovery yield: Preferably, the previously obtained high-isomaltodextrin-isomaltose fraction, the feed sugar solution, and the previously obtained high-isomaltose-glucose fraction may be applied successively to the column in the given order.

Although the high-isomaltose fraction thus obtained may be used intact without further processing, it may be, if necessary, treated as follows: The fraction may be subjected to conventional purification steps, e.g., filtration, decolorization and/or deionization, and the purified product may be concentrated to obtain a syrup which can be spray-dried into powder.

The high-isomaltose fraction with an isomaltose content of 40% or higher can be advantageously usable as a sweetener, filler, moisture-retaining agent, or vehicle in various food products, cosmetics, or pharmaceuticals; or to impart them with an appropriate thickness, viscosity and/or gloss, or prevent the retrogradation of their amylaceous constituents, in addition to the use as a starting material for producing isomaltitol.

The following experiment explains the present invention in more detail.

EXPERIMENT

Material sugar solution

A 60 w/w % aqueous solution of glucose was subjected to the action of an immobilized glucoamylase, prepared by the method as disclosed in Japan Kokai No. 124,494/80, at 50° C. and pH 4.8 to effect reversible reaction of glucose. In the course of the reaction, small portions of the reaction mixture were periodically collected, diluted to give respective concentrations of 45 w/w %, and used in the following experiment as the feed sugar solutions. The sugar compositions of the material sugar solutions are given in TABLE I.

"Dowex 50WX4 (Na+)", a commercially-available strongly-acidic cation exchange resin of alkali metal-form, a product of Dow Chemical Company, Midland, Mich., U.S.A., in an aqeous suspension, was packed in a jacketted stainless steel column, inside diameter, 5.4 cm, to give a bed depth of 10 m.

While keeping the temperature in the column at 75° C., each of the material sugar solutions as listed in TABLE B was applied thereto in an amount of 5 v/v % against the bed volume, and then fractionated by charging thereto 75° C. hot water at a flow rate of SV 0.2, followed by the harvest of the high-isomaltose fraction with an isomaltose content of 40% or higher. The results are given in TABLE II.

TABLE I

| Feed sugar solution (No.) | Sugar composition (%) | | |
|---|---|---|---|
| | Glucose | Isomaltose | Isomaltotriose and higher isomaltodextrins |
| 1 | 98.6 | 1.1 | 0.3 |
| 2 | 95.7 | 3.6 | 0.7 |
| 3 | 91.1 | 7.1 | 1.8 |
| 4 | 83.3 | 12.7 | 4.2 |
| 5 | 63.0 | 25.5 | 11.5 |

TABLE II

| A | B | C | D |
|---|---|---|---|
| 1 | 1.1 | impossible | impossible |
| 2 | 3.6 | 9.9 | 45.2 |
| 3 | 7.1 | 32.5 | 75.3 |
| 4 | 12.7 | 62.2 | 80.6 |
| 5 | 25.5 | 126.2 | 81.4 |

Note:
Column A is the feed sugar solution number described in TABLE II; Column B is the content of isomaltose in each solution expressed as a percentage; column C is the yield of isomaltose in the high-isomaltose fraction expressed in grams; column D expresses the isomaltose yield expressed as a percentage of the isomaltose constituent in the feed sugar solution; the designation "impossible" means that no high-isomaltose fraction with an isomaltose content of 40% or higher was obtained.

The experimental results, as shown in TABLE II, confirm that the isomaltose content in the feed sugar solution is 7% or higher, a high-isomaltose fraction with an isomaltose content of 40% or higher is easily obtainable in an extremely higher recovery yield, i.e., 70% or higher, against the isomaltose constituent in the feed sugar solution.

Several embodiments of the present invention are disclosed hereinafter.

EXAMPLE 1

In this example, a 45 w/w % aqueous solution of a reversible-reaction product with an isomaltose content of 25.5%, obtained similarly as in the experiment, was used as a feed sugar solution.

"XT-1022E (Na+)", a commercially-available strongly-acidic cation exchange resin of alkali metal-form, a product of Tokyo Chemical Industries, Kita-ku, Tokyo, Japan, in an aqueous suspension, was packed in four jacketted stainless steel columns, inside diameter, 5.4 cm, to give respective bed depths of 5 m, and the columns were cascaded to give a total bed depth of 20 m.

While keeping the temperature in the columns at 75° C., the material sugar solution was applied thereto in an amount of 5 v/v % against the bed volume, and then fractionated by charging thereto 75° C. hot water at a flow rate of SV 0.13, followed by the harvest of the high-isomaltose fraction with an isomaltose content of 40% or higher.

The high-maltose fraction contained 233 g isomaltose, and the recovery yield was extremely high, i.e., 75.1%, against the isomaltose constituent in the feed sugar solution.

Thereafter, the fraction was decolorized, and deionized, in usual way, to obtain 580 g of a syrup with a moisture content of 15%. The syrup thus obtained contained 46.4% isomaltose, and 43.0% isomaltodextrins including isomaltotriose and isomaltotetraose.

EXAMPLE 2

After dissolving dextran in 1N sulfuric acid to give a concentration of 20 w/w %, the solution was kept at 100° C. for 60 minutes, and neutralized with 6N sodium hydroxide solution. The resultant mixture solution was then purified with ion exchange resins of H- and OH- forms, and concentrated to obtain 60 w/w % aqueous material sugar solution with an isomaltose content of 12.2%.

The resin, used in example 1, was converted into $K^+$-form in the usual way, and packed in a jacketted stainless steel column, inside diameter, 6.2 cm, to give a bed depth of 10 m.

While keeping the temperature in the column at 60° C., the material sugar solution was applied thereto in an amount of 3 v/v % against the bed volume, and then fractionated by charging thereto 60° C. hot water at a flow rate of SV 0.2, followed by the harvest of the high-isomaltose fraction with an isomaltose content of 40% or higher.

The fraction contained 66.0 g isomaltose, and the recovery yield was extremely high, i.e., 79.1%, against the isomaltose constituent in the material sugar solution. Thereafter, the fraction was purified, and concentrated, similarly as in example 1, to obtain 170 g of a syrup with a moisture content of 15%.

The syrup thus obtained contained 43.2% isomaltose, and 48.6% isomaltodextrins including isomaltotriose and isomaltotetraose.

EXAMPLE 3

A 45 w/w % aqueous solution of corn syrup was added with an immobilized glucoamylase, prepared similarly as in experiment, and the mixture was incubated at 50° C. and pH 4.8 to effect reversible reaction of the glucose constituent, obtaining a feed sugar solution with an isomaltose content of 16.5%.

"Dowex 50WX4 ($Na^+$)", a commercially-available strongly-acidic cation exchange resin of alkali metal-from, a product of Dow Chemical Company, Midland, Mich., U.S.A., in an aqueous suspension, was packed in fresh columns of the same material and dimensions as used in example 1 to give a total bed depth of 15 m.

While keeping the temperature in the columns at 55° C., the material sugar solution was applied thereto in an amount of 6.6 v/v % against the bed volume, and fractionated by charging thereto 55° C. hot water at a flow rate of SV 0.13, followed by the harvest of the high-isomaltose fraction with an isomaltose content of 40% or higher.

The fraction contained 156 g isomaltose, and the recovery yield was extremely high, i.e., 78.1%, against the isomaltose constituent in the feed sugar solution.

Thereafter, the fraction was purified, and concentrated similarly as in example 1. The resultant concentrate was dried in vacuo, and spray-dried to obtain 320 g of a powder with a moisture content of below 1%.

The powder thus obtained contained 47.7% isomaltose, and 20.3% isomaltodextrins including isomaltotriose and isomaltotetraose.

EXAMPLE 4

A 45 w/w % aqueous solution of a reversible-reaction product with an isomaltose content of 25.5%, obtained similarly as in experiment, was used as the feed sugar solution.

In this example, a dual-stage fractionation was carried out. The first fractionation was carried out as follows: Similarly as in example 1, the feed sugar solution was applied to a column, and then fractionated, except that the solution was applied in an amount of 20 v/v % against the bed volume. Fractions A through E were obtained, respectively designated high-isomaltodextrin fraction, high-isomaltodextrin-isomaltose fraction, high-isomaltose fraction, high-iso-maltose-glucose fraction, and high-glucose fraction, the elution being effected in the given order. Fraction C, the high-isomaltose fraction, was collected, and Fractions A and E were removed from the fractionation system.

The additional fractionation was carried out as follows: The column was applied successively with Fraction B, the feed sugar solution in an amount of about 10 v/v % against the bed volume, and Fraction D, in the given order, and then charged similarly as in example 1 with 75° C. hot water to effect fractionation, followed by the harvest of the resultant high-isomaltose fractions with an isomaltose content of 50% or higher. The additional fractionation was repeated up to 50 batches in total, and the averaged results per batch were calculated. On an average, one high-isomaltose fraction contained 519 g isomaltose, and the recovery yield was extremely high, i.e, 83.7%, against the isomaltose constituent in the material sugar solution.

Fifty high-isomaltose fractions were pooled, and treated similarly as in example 3 to obtain 43 kg of a powder. The powder contained 58.4% isomaltose, and 29.3% isomaltodextrins including isomaltotriose and isomaltotetraose.

Fractions A and E, which had been removed from the fractionation system, were concentrated to give a concentration of about 60 w/w %, and the resultant concentrate was subjected to the action of enzymatic action of the immobilized glucoamylase to obtain a similar sugar composition as that in the material sugar solution, confirming that the reaction mixture can be used as a material sugar solution in the invention. It was also confirmed that the use of the reaction mixture results in a substantially-complete conversion of material glucose into the objective isomaltose.

EXAMPLE 5

An 60 w/w % aqueous solution of a reversible-reaction product with an isomaltose content of 25.5%, obtained similarly as in the experiment, was used as a feed sugar solution.

"Amberlite CG-120 ($Ca^{2+}$)", a commercially-available strongly-acidic cation exchange resin of alkaline earth metal-form, a product of Rohm & Haas Company, Philadelphia, Pa., U.S.A., in an aqueous suspension, was packed in fresh columns of the same material and dimensions as used in example 1 to give a total bed depth of 10 m.

Also, in this example, a dual-stage fractionation was carried out. The first fractionation was carried out as follows. While keeping the temperature in the columns at 80° C., the feed sugar solution was applied thereto in an amount of 15 v/v % against the bed volume, and then fractionated by charging thereto 80° C. hot water at a flow rate of SV 0.6 to obtain a similar elution to that of Example 4.

Fraction C, the high-maltose fraction, was collected, while Fractions A and E were pooled, and concentrated to give a concentration of about 60 w/w %. The resultant concentrate was then subjected to the enzymatic action of the immobilized glucoamylase to obtain a similar sugar composition as that in the feed sugar solution, and the resultant reaction product was used as a feed sugar solution.

The additional fractionation was carried out as follows: The column was further applied successively with Fraction B, the feed sugar solution in an amount of about 7 v/v % against the bed volume, and Fraction D, in the given order, and charged with 80° C. hot water at a flow rate of SV 0.6 to effect fractionation, followed by the harvest of the resultant high-isomaltose fractions with an isomaltose content of 60% or higher.

The FIGURE shows the flow-chart of the process in this example, where Fractions A through E designate the elution fractions; G, glucose; GA, enzymatic reaction step by glucoamylase; S, feed sugar solution; R, fractionation step by resin; V, concentration step; and P, high-purity isomaltose product.

The additional fractionation was repeated up to 200 batches in total, and the averaged results per batch were calculated. On an average, one high-isomaltose fraction contained 256 g isomaltose, and the recovery yield was extremely high, i.e., 83.4%, against the isomaltose constituent in the material sugar solution. Two-hundred high-isomaltose fractions were pooled, and treated similarly as in example 3 to obtain 77 kg of a powder. The powder contained 65.3% isomaltose, and 22.7% isomaltodextrins including isomaltotriose and isomaltotetraose.

We claim:

1. A process for the separation of isomaltose from a feed solution by the utilization of an ion exchange resin, comprising:
   (a) providing a feed solution containing at least 7% isomaltose based on the weight of the dry solid, the remainder consisting essentially of glucose and isomaltodextrins;
   (b) sequentially admitting predetermined volumes of the feed solution and water to a column of a strongly acidic cation exchange resin having sulphonyl groups of an alkali metal or alkaline earth metal form;
   (c) sequentially separating the effluents from the column into the following fractions:
      a first fraction rich in isomaltodextrins,
      a second fraction rich in isomaltodextrins, but highly contaminated with isomaltose,
      a third fraction rich in isomaltose,
      a fourth fraction rich in isomaltose, but highly contaminated with glucose, and
      a fifth fraction rich in glucose;
   (d) recovering the third fraction rich in isomaltose;
   (e) sequentially admitting into the column:
      the second fraction obtained in the step (c),
      a feed solution having an isomaltose content of at least 7% based on the weight dry solid, and the remainder consisting essentially of glucose and isomaltodextrins;
      the fourth fraction obtained in the step (c) and water; and
   (f) repeating steps (c), (d) and (e) in a cyclic manner.

2. A process in accordance with claim 1, wherein the isomaltose content in the third fraction is 40% or higher, based on the weight of the dry solid.

3. A process in accordance with claim 1, wherein the bed depth of the column is at least 7 m.

4. A process in accordance with claim 1, wherein the temperature of the column of the resin is kept at 45°–85° C.

5. A process in accordance with claim 1, wherein the cation exchange resin is in the form of $Na^+$, $K^+$, $Ca^{2+}$ or $Mg^{2+}$.

6. A process in accordance with claim 1, wherein the concentration of the feed solution is in the range of 10–70 w/w % on the basis of dry solid.

7. A process in accordance with claim 1, wherein the water is admitted to the column at a flow rate of SV 0.1–2.0.

8. A process in accordance with claim 1, wherein the nominal particle size of the cation exchange resin is in the range of 0.01–0.5 mm.

9. A process in accordance with claim 1, wherein the feed solution is an aqueous solution of a reversible-reaction product containing at least 7% isomaltose on the weight of the dry solid, which has been obtained by:
   providing a 40–80 w/w % aqueous solution of a member selected from the group consisting of glucose, maltose, maltodextrin, corn syrup, dextrin and mixtures thereof; and
   exposing the aqueous solution to an effective amount of glucoamylase.

10. A process in accordance with claim 1, wherein the feed solution is an aqueous solution of a glucose-transferred product containing at least 7% isomaltose on the weight of the dry solid, which has been obtained by:
   providing an aqueous solution of a member selected from the group consisting of maltose, maltodextrin, corn syrup, dextrin and mixture thereof; and
   exposing the aqueous solution to an effective amount of α-glucosidase.

11. A process in accordance with claim 1, wherein the feed solution is an aqueous solution of a partial dextran hydrolysate, which has been obtained by:
   providing an aqueous solution of dextran;
   exposing the aqueous solution to an effective amount of an acid catalyst; and
   neutralizing the reaction mixture.

12. A process in accordance with claim 1, wherein the feed solution is an aqueous solution of a partial dextran hydrolyzate, which has been obtained by:
   providing an aqueous solution of dextran; and
   exposing the aqueous solution to an effective amount of dextranase or isomaltodextranase.

* * * * *